United States Patent [19]
Robertson

[11] Patent Number: 5,206,151
[45] Date of Patent: Apr. 27, 1993

[54] RAPID SELECTION OF BIOCIDE USING A REDUCTION OXIDATION INDICATOR SYSTEM

[75] Inventor: Linda R. Robertson, St. Charles, Ill.

[73] Assignee: Nalco Chemical Company, Naperville, Ill.

[21] Appl. No.: 536,390

[22] Filed: Jun. 11, 1990

[51] Int. Cl.$^5$ .................. C12Q 1/00; C12Q 1/02; C12N 5/00
[52] U.S. Cl. ........................... 435/32; 435/4; 435/29; 435/240.3
[58] Field of Search ............ 435/4, 29, 32, 240.3

[56] References Cited
FOREIGN PATENT DOCUMENTS
1535643 10/1977 United Kingdom .

OTHER PUBLICATIONS

Otsuka, J. Dairy Science, vol. 52, No. 12, pp. 2041–2045, 1969 "Resazurin Test Paper Method for Determining the Sanitary Quality of Raw Milk".
Kull, Applied Microbiology, vol. 9, pp. 538–541, 1961.
Staneck et al., J. Clinical Microbiology, vol. 26, No. 1, pp. 1–7, 1988.
"Rapid Biocide Selection" by Clark and Wildman, by Buckman Labs, Memphis, Tenn., Proceedings of the Technical Association of the Pulp and Paper Industry 1984 Research & Development Conference, pp. 121–124, copyright 1984, TAPPI.
Bull. Environm. Contam. Toxicol., vol. 26, pp. 145–149 (1981) "A Rapid Biochemical Test for Measuring Chemical Toxicity" by D. Liu.
Kirk–Othmer Encyclopedia of Chemical Technology, Third Edition, vol. 15, pp. 550–553, copyright 1981, John Wiley and Sons, Inc.
Chemical Abstracts, vol. 110, p. 89:9923a "Effect of Biocides and Paper Auxiliaries on Reductase Test".
The Merck Index, An Encyclopedia of Chemicals, Drugs, and Biologicals, Tenth Edition, 1983, p. 1174, paragraph 8037.Resazurin.
Methods in Enzymology, vol. 41, Part B, 1975, p. 53 in sequence, "Fluorometric Determination of Dehydrogenase Activity Using Resorufin", by Guilbault.
Wochenbl. Papierfabr., 116(11/12): 469–72 (Jun. 15, 1988), "Effect of Biocides and Auxiliary Agents on the Reductase Test", by A. Jakob, Institute of Paper Chemistry, Appleton, Wis.

(List continued on next page.)

Primary Examiner—Michael G. Wityshyn
Assistant Examiner—Jane A. Williams
Attorney, Agent, or Firm—Robert A. Miller; James J. Drake

[57] ABSTRACT

A rapid method for determining the minimum inhibitory concentration of biocides or biocidal agents for use in various microbiological contaminated aqueous systems is disclosed. This rapid technique provides for an opportunity to determine the minimum amount of antimicrobial agents, or biocides either singularly or combination, to control microbiological growth in aqueous streams contaminated by microorganisms. The test involves the use of reduction oxidation indicator dye systems which react to enhanced microbiological activity producing reducing enzymes such as dehydrogenase enzymes. The technique provides an answer within a time period of from about 30 minutes to about 8–10 hours as opposed to normal testing procedure that can require up to 1–2 weeks. The test procedures uses multiple columns of multiple sample wells on a microtitration plate and techniques for transferring prescribed aliquots of contaminated aqueous systems, nutrients, redox indicator dyes, and incremental and serially diluted concentrations of anti-microbial agents.

11 Claims, 5 Drawing Sheets

OTHER PUBLICATIONS

Bulletin of Environmental Contamination Toxicology (1986) 36:60-66, "Biochemical Responses of Bacteria after Short Exposure to Alkyltins", by Liu et al.

First Call for Papers for: The First Biennial Water Quality Symposium, Banff Alberta Canada, Aug. 29–Sep. 2, 1988, Analytical Procedures by Liu, pp. 254–257.

"A Direct Resazurin Test for Measuring Chemical Toxicity" by Thomson et al., in "Toxicity Assessment: An International Quarterly", vol. 1, pp. 407–418 (1986).

Environmental Toxicity and Chemistry, vol. 2, pp. 185–193, 1983, "Applicability of Microbial Toxicity Assays to Assessment Problems" by Gillett et al.

Arch. Environ. Contam. Toxicol., vol. 14, pp. 659–667 (1985), "A Comparison of Three Microbial Assay Procedures for Measuring Toxicity of Chemical Residues", Greene et al.

Nature, No. 3935, Mar. 31, 1945, "Oxidation—Reduction Aspects of Resazurin" by Twigg.

Water Treatment Institute Newsletter, vol. 1, No. 42 "Rapid Biocide Selection" by Clark, IWC-86-38, pp. 1–5.

FIG. 5

RAPID SELECTION OF BIOCIDE USING A REDUCTION OXIDATION INDICATOR SYSTEM

INTRODUCTION

In many areas of industrial water use, biocides must be used to control bacterial growth to avoid, prevent or control microbiological accumulation of bacterial deposits and accumulation of the byproducts derived therefrom. The presence of these bacterial and other microbiological organisms often interfere with water processing or manufacturing of various products where these various industrial waters are being used. Industrial waters may include various waters such as those circulating in once through cooling water systems, waters recirculating in a closed loop cooling water system with or without a blow down feature, waters used and collected for processing prior to their use in industrial processes, waters being discharged as effluent waters both before or after treatment to meet specified water quality standards, process waters used in the manufacture of various products, for example of paper or textile products, and other process waters such as those waters used in recovery of crude oil or in the processing of hydrocarbon chemicals.

In each of the uses of industrial waters, biocides have been and are being used presently to reduce, prevent, and control the presence of microorganisms and detrimental bacteria and similar growing organisms. Not only do these growths cause fouling, but their presence may also lead to corrosion of metal surfaces on which these microbiological colonies are deposited.

In the use of various biocides, a process is involved which includes the addition of a biocide into the industrial water being treated in such strength so as to control the growth of these microbiological organisms. By controlling the growth we mean to include not only total elimination of biological growth and elimination of the microorganism, but also static control of microorganism population so that extremes in growth population are controlled though not all organisms are killed. In the process of testing and determining the efficiency and type of biocide to be used, often procedures are required which last for from 24 to about 48 hours, and sometimes for 1 week and up to 2 weeks or more to determine the efficacious use of a particular biocide and particularly to determine the amount of that biocide which is necessary to reach static control or total elimination of the particular microorganisms being treated in the particular industrial water environment in which these organisms occur.

These long test periods are not only time consuming but wasteful of resources and the tests are expensive in regard to the determination of the proper biocide and its strength and concentration of optimal use to maintain microbiological control of a particular contaminated industrial source.

It is therefore an object of this invention to provide for a quick method to screen various and multiple microbicides and/or toxicants useful in treating industrial waters to provide microbiological control and especially in treating those industrial waters used in the process of paper making.

It further is an object of this invention to provide for a quick visual screening procedure to screen and test toxicants and biocides useful in control of microorganism growth and provide for control or elimination of microorganism growth in industrial waters, particularly in the process of manufacturing paper.

It is further an object of this invention to use in the visual procedure, certain reduction oxidation indicators (often called redox indicator dyes) which change color in the visual spectrum such that a determination of the minimal inhibitory concentration (or MIC) of a particular antimicrobial agent in an aqueous system contaminated by microbiological organisms can be made.

It is a further object of this invention to provide for an easily handled microtitration plate containing multiple sample cells, (or sample wells) each cell being capable of holding a determined volume or aliquot of the contaminated aqueous system. To this aliquot of aqueous sample is then added a known and prescribed amount of a reduction-oxidation indicator dye capable of reacting with chemical reducing agents formed by increased metabolic rates of microbiological systems which reducing agents can include, but are not necessarily limited to, reducing enzymes, such as, but not limited to, dehydrogenase enzymes. A chemical reaction between, for example, the reducing enzymes formed at increased metabolic rates and the reduction-oxidation indicator dye compounds then produces a change in the color of this indicator dye which is a measure of the increased microbiological metabolism caused by adding nutrients to the aqueous aliquot contained in the samples wells of the microtitration plates. These multiple aliquots then are tested (visually observed) for color changes. The object of the invention also include procedures designed to determine, through a series of controlled dilutions giving various concentrations of antimicrobial agents to determine the minimal inhibitory concentrations of a particular antimicrobial agent or biocide or any combination of these antimicrobial agents or biocides in a particular contaminated aqueous system, for example a certain paper furnish, or waters used in the manufacture of paper.

THE INVENTION

I have invented a method of determining the minimum inhibitor concentration (MIC) of an antimicrobial agent in contaminated aqueous media containing microbiological organisms, which method comprises the steps;

(a) obtaining a known volume aliquot of the contaminated aqueous system;

(b) adding thereto a known amount of an oxidation reduction indicator dye, which indicator dye is capable of reacting with dehydrogenase enzymes produced by said microbiological organisms;

(c) adding thereto sufficient nutrients capable of accelerating microbiological organism activity, thereby forming a reaction product between reducing enzymes and the oxidation-reduction indicator dye; and then, (d) obtaining multiple aliquots of the indicator dye treated, nutrient treated, aqueous system and transferring each said multiple aliquot to a microtitration plate containing multiple sample wells, each well containing but one of the multiple aliquots, and then;

(e) adding to at least one column of these sample wells on said titration plate a serially diluted amount of at least one antimicrobial agent, provided that a single column is treated with only one said antimicrobial agent; and further provided that at least one column is left untreated; thereby forming a treated titration plate;

(f) and then incubating said treated titration plate at a temperature essentially equivalent to the temperature of the contaminated aqueous system from which the aliquot was originally taken for a period of time sufficient to develop the change in the indicator dye color by the reaction of the indicator dye with reducing enzymes produced by nutrient acceleration of microbiological metabolism; and then (g) comparing the first change in color in dye relative to the untreated column to determine the minimum inhibitor concentration of antimicrobial agent which inhibits growth of microbiological organism contained in said contaminated aqueous system.

By the anti microbial agent we mean to include an agent containing one or a blend of one or more biocides. These biocides are later described in our process. The contaminated aqueous system is chosen from the groups consisting of stock or furnish fiber dispersions or other aqueous solution from pulp and paper manufacture, open recirculation cooling water system, waste effluent streams, chemical process waters and processed streams, fermentation streams, and the like.

In our choice of reduction oxidation indicator dyes, the indicator dye preferably chosen is from the resazurin redox couple which consists of resazurin, resorufin and hydroresorufin. These chemical structures are provided below:

Oxidized form.
$C_{12}H_7NO_4$

Resazurin (slate blue)

Reduced forms.
$C_{12}H_7NO_3$

Resorufin (pink)

$C_{12}H_8NO_3$

Hydroresorufin (colorless)

In the above description, our process takes advantage primarily of only the first reduction of resazurin to resorufin. However, in a high population of microorganisms, in the absence of sufficient inhibiting amounts of antimicrobial agent(s), the reducing chemicals produced by nutriated microorganisms can drive this reduction all the way to hydro-resorufin, which is colorless. In addition to the above reduction oxidation indicator dye/system, other indicator dyes may also be used. These compounds include the following:

(1) Tetrazolium Violet
(2) 2-(p-Iodophenyl)-3-(p-nitrophenyl)-5-phenyl-tetrazolium chloride
(3) Methylene Blue
(4) Formazan Dyes As described, the preferred reduction oxidation indicator dye is Resazurin. Also useful is formazan dyes systems which form highly colored compounds which are easily visualized spectrophotometrically.

The resazurin dyes are coupled with resorufins to form the reduction oxidation indicator dye system. The color of the oxidized form of this indicator dye is blue and when reduced, changes to a pink color. If highly intense reducing compounds are present this pink color can be changed to a clear colorless solution.

NUTRIENTS

The nutrients which may be added to the aliquot samples treated with the reduction oxidation indicator dyes described above include any nutrient in solution or suspension with water or any base nutrient mix which includes glucose, sucrose, fructose, beef extract, peptone, (the combination of beef extract and peptone is often called "nutrient broth") tryptone, milk, half and half cream, yeast extract, or any mixture of the above. The specific nutrients to be preferred in the use of our rapid method to determine the minimum inhibitory concentration (MIC) of a particular antimicrobial agent is a mixture of glucose, nutrient broth and half and half cream in the volume ratio of approximately 1 to 8 to 10. However these nutrients may be blended in any reasonable ratios one to the other and successfully accelerate microbiological organism activity which in turn accelerates the metabolism rates and formation of reducing compounds, for example the dehydrogenase enzymes which may in turn react with the reduction oxidization indicator dyes of this invention. By adding the nutrients to the solutions directly on the microtitration plate, microbial activity or microbial respiration is increased and metabolism rates or metabolic processes of the microorganism increases to provide the results above. Therefore the interaction of these reducing chemicals and enzymes with the redox indicator dyes provides for monitoring cell viability via the organisms cellular electron transfer system.

MICROTITRATION PLATES

The microtitration plates used are preferably clear plastic plates which contain multiple columns of depressions, called sample wells and multiple wells in each column. Most preferably the microtitration plate contains at least two columns of at least three samples wells in each column. Preferably the microtitration plate contains from about 6 to about 12 columns, each column containing from about 6 to 12 sample wells. However, these plates may also be, for example, white ceramic plates, or any other plate-like construction of proper background to provides easy reading or visualization of color changes. These plates may be obtained from Costar Corporation, Cambridge, Mass.

PROCEDURE

Into an upper series of sample wells running transversely across the multiple columns of the microtitrations plate are added equal volumes of aliquots from the aqueous system being tested. To these same series of sample wells are added a prescribed concentration of redox indicator dye, nutrient and antimicrobial agent. The antimicrobial agent is added at a concentration ranging from about 0.1 parts per million in concentration up to about 5,000 parts per million. Then by using multiple pipettes, serially diluted amounts of antimicrobial agent having concentrations of antimicrobial agents ranging from about 0.1 parts per million to about 5,000 parts per million are added to each of the sample wells in each of the columns thereby achieving sample wells containing the biologically contaminated test waters and a serially diluted amount of antimicrobial agent in each of the sample wells in each column. Either before or after the antimicrobial agent a known amount of a reduction oxidation indicator dye, preferably resazurin, is added to each sample well and a known amount of a nutrient media is also added thereto. This obtains a series, in each column, of sample wells containing a serially diluted sequence of equal aliquots of the contaminated aqueous system to which ever decreasing amounts of antimicrobial agent has been added. This series of decreasing amounts of antimicrobial agent, in the presence of nutrients and a reduction oxidation indicator dye then measures microbiological or metabolic activity reflecting increased activity of the organisms cellular electron transfer system. Each column tests a different biocide against the microbiological organisms contained in the aliquot sample of nutrient treated media.

This titration plate containing separate columns of multiple sample wells, which sample wells in turn contains serially decreasing concentrations of antimicrobial agent in equal aliquots of microorganism and equal amounts of nutrient and reduction oxidation indicator dye is then incubated at temperatures which may be essentially equivalent to the temperature of the contaminated aqueous system from which the microbiological organisms contaminated samples were originally obtained. Essentially equivalent temperatures is meant to include actual environment temperature plus or minus about 10°-15° C. These incubation temperatures are at least 20° C. but normally do not exceed about 80° C. This incubation is for a period of time sufficient to develop the change in the indicator dye color through the reaction of the indicator dye with the dehydrogenase produced by nutrient accelerated microbiological organism activity in the test media.

This incubator time period may be as little as approximately 30 minutes and may be as long as from 8-10 hours. This testing time, preferably about 4 to about 8 hours, is considerably shorter in time and considerably more sensitive to the presence of minimum inhibitory concentrations of antimicrobial agents than previous tests for antimicrobial activity. After an appropriate incubating time of between approximately 30 minutes and 8-10 hours, the titration plate is removed and visually examined to determine color changes which have occurred in each of the sample wells in each of the columns of the titration plate. The minimum inhibitory concentration of antimicrobial agent contained in each column is determined at that level of concentration where the first color change is observed going from a lower to a higher concentration of antimicrobial agent in that column. Of course, each column contains a separate antimicrobial agent (or biocide) or separate mixture thereof.

The process may be repeated using different initial concentrations of antimicrobial agent until repeated experiments confirm the minimum inhibitor concentration which will control and maintain control of microbiological organisms in the aqueous media being treated with the antimicrobial agent.

Preferably in each column a single antimicrobial agent is tested at the various concentrations. These concentrations are provided by the serial dilution described above. The steps of providing for nutrient concentrations and providing for concentrations of reduction oxidation indicator dye may be performed in any sequence after any of steps a, d, and e above. That is, steps b and c are performed in any sequence after either of steps a, d, or e. As described above the reduction oxidation dyes are preferably resazurin and its various reduced forms, but may also include tetrazolium violet and 2-(p-Iodophenyl)-3-(p-nitrophenyl)-5-phenyl-tetrazolium chloride. These so called redox indicator dyes are readily available commercially.

It is preferred that the pHs of the aqueous systems being tested with the resazurin dyes are adjusted between a pH ranging from about 4 to about 9, and preferably between a pH of about 5 to about 8. Most preferably, the pH should be adjusted to a pH of from 6.0-8.0. However it is most preferable that the tests performed be done at the pH of the aqueous system in which the microorganisms are surviving. If these pH's are below about 6.0, other dyes, such as tetrazolium violet or 2-(p-Iodophenyl)-3-(p-nitrophenyl)-5-phenyl-tetrazolium chloride can be used. These dyes are less sensitive to pH changes.

Our method of determining minimum inhibitory concentration of antimicrobial agents is particularly found useful where the contaminated aqueous systems being tested are stock or furnish waters obtained from various locations in a pulp and paper manufacturing mill. Preferably the redox indicator dyes are dyes chosen from the groups consisting of tetrazolium violet, 2-(p-Iodophenyl)-3-(p-nitrophenyl)-5-phenyl-tetrazolium chloride, and resazurin. The nutrients are preferably chosen from nutrient broth, glucose, dairy half and half ultra pasteurized creamer, and mixtures thereof, which mixture may also include the other nutrients described above. The microtitration plate contains at least three, preferably four columns of at least four and preferably at least eight sample wells each. The microtitration plate are normally made of glass, ceramic, but are preferably clear plastic or any other media which may tolerate the incubation temperatures and time periods and which provide a reasonable background on which colors can be observed and interpreted. The treated titration plate is normally incubated at temperatures ranging from about 30° C. to about 50° C. for a period of time ranging from about 30 minutes to about 4 to 6 hours.

In addition the incubation may be completed in an air atmosphere containing oxygen or it may be completed in an inert gas atmosphere such as that atmosphere provided by Nitrogen, Helium, argon, carbon dioxide or the like. When the incubation is performed under inert gas atmosphere additional results may be obtained which can give the operator information in regard to the response of organisms to biocides under anaerobic conditions contaminated aqueous systems. These systems may be anaerobic as well as aerobic in character.

To provide further information about our method for determining minimum inhibitor concentration of antimicrobial agents in contaminated aqueous systems, the following examples are given.

EXAMPLES

Approximately 100 ml. of filtered paper furnish either from stock furnish, tissue furnish, or the like, are obtained. The pH of this solution is adjusted to a minimum pH of 6.5 or above. Preferably if the microtitration plate is to be incubated in an anaerobic environment such as under a carbon dioxide atmosphere, approximately 1.01 grams each of sodium phosphate dibasic and potassium phosphate monobasic are added to the filtered stock furnish to buffer the water solution to a pH of about 7.0. These filtered solutions, which are filtered through a coarse filter, such as through tissue paper or a filter having a mesh size of about US Std Sieve Series No. 80, then have approximately 5 ml. of a resazurin solution added thereto. The resazurin solution contains 1.1 mg resazurin and 100 ml. of a nutrient broth which contains 0.8 gm dry powder from a BBL or Difco growth media and 0.1 gm dextrose. To this solution is added 2 ml of ultra pasteurized half and half creamer which may be obtained at a local grocery. Approximately 150 microliters of this treated filtered water furnish solution is then pipetted into each of the microtitration sample wells using a multi-channel micropipette, such as supplied by Flow Laboratories as their Titertek ®* and in as many columns as there are biocide preparations to be tested.
*Titertek is aregistered trademark of Flow Laboratories Into a separate container approximately 4 ml. of the filtered aqueous solution above are added. One ml of a 1 per cent biocide solution of a commercial or test biocide product also is added to the container and the solutions are mixed by swirling. This forms a 2000 ppm solution of biocide in the test solution to which has been added nutrient, if needed, and pH buffering chemicals.

These commercial or test biocidal agents can include, but are not necessarily limited to, polyamines, isothiazolins, organosulfurs, quaternary amines, organobromines, carbamates, methylene bis thiocyanate, or combinations thereof, or any other additional biocidal agents known.

Immediately after forming this 2000 ppm. solution, 150 microliters of this treatment solution are removed and placed in a first micro sample well of the first test column of the microtitration plate. One column is left untreated by biocide. The solution formed in the microtitration sample well is then drawn up into the pipette used to transfer the biocide solution 2 to 3 times and placed back into the same sample well, thereby mixing the solutions. After mixing, 150 microliter of the mixture is removed from this first sample well and dispensed into the next lower sample well in the same column. Again the mixing procedure occurs and a final removal of 150 microliter of this second sample well solution is removed by using the micro pipette. This second aliquot in this series is placed in a third sample well (in the same column) on the microtitration plate. This procedure is repeated until all of the sample wells in a single column contains serially diluted concentrations of antimicrobial agent (biocide) added thereto and mixed therewith. The last 150 microliter aliquot taken from the last of the sample wells in the column is discarded.

This procedure is repeated in each column for all biocides to be tested. One column of sample wells is left untreated to act as a blank, that is, a test column containing test solution, nutrient, redox dye, but without any addition of biocidal or antimicrobial agents.

The microtitration plates containing multiple columns of multiple sample wells are then incubated. If the incubation is to the aerobic, the sample wells are covered preferably with clear plastic sheeting, for example, a clear adhesive tape such as scotch ®** brand tape may be placed on each column of sample wells, and incubated either in the presence of a light source or in the absence of a light source, at the chosen temperatures. These temperatures are preferably those temperatures occurring with the process stream being tested, plus or minus from about 10°–15° C. These temperatures usually range from about 20° C. to about 80° C. and are usually from about 25°–30° C. to approximately 50°–60° C. If the microtitration plate is to be incubated in a carbon dioxide environment, i.e. anaerobically, the plate is placed in an anaerobic environment such as provided, for example, by a BBL GasPak Pouch TM before incubation. This commercially available gas pack provides for conversion of oxygen in the air over the sample to carbon dioxide thereby providing for a $CO_2$ atmosphere predominantly in the presence of nitrogen, providing a nitrogen/carbon dioxide environment.
**Scotch ® is a registered trademark of the 3M Company Following the above procedures, the concentration gradient, i.e., the serially diluted concentration of antimicrobial agents, will range from about 1000 parts per million in the first high concentration sample well to approximately 8 parts per million (or below) in the lowest concentration sample well. In the presence of resazurin dyes, the sample wells which do not contain sufficient concentration of antimicrobial agent to inhibit microbial metabolism will be pink in color. Those sample wells which contain sufficient concentration of antimicrobial agent to inhibit microbiological activity will be a blue color. By comparing the concentrations in the serially diluted sample wells, the MIC for each antimicrobial agent can be determined visually at the sample well where the lowest concentration of antimicrobial agent which controls growth of microbiological organisms in the sample tested occurs. This is the lowest concentration which appears blue in color, when using resazurin.

A cautionary word in the use of this rapid screening technique should include the fact that some antimicrobial agents or biocides are themselves reducing agents and can, at high concentration, cause the reduction oxidation indicator dyes, such as resazurin, to turn to pink due to a chemical side reaction. If, at high concentrations of antimicrobial agents, the sample wells are observed to be pink after being incubated, and the next successive well remain blue, for example such that the well at 1000 parts per million biocide is pink, the well at 500 parts per million biocide is blue, the well 250 parts per million is blue, the well at 125 parts per million, the well at 62 parts per million is blue, and the well at 31 parts per million is pink then the minimum inhibitory concentration under this circumstance is determined from the first change of pink color to blue color at the lower end of the serial concentration gradient. This is only true when the antimicrobial agents or biocides being used are reducing agents in their own right.

In a paper mill certain aqueous systems or paper furnishes have extremely high concentrations of reducing agents such as when the paper furnish has a sulfite residual. In this situation it is desirable to titrate the excess reducing agents, for example, the excess sulfite, with a percent glyoxal solution, thereby reducing or eliminating the chemical reducing agents without effecting microbiological activity. This technique is preferable if used to remove $\leq 50$ ppm sulfites. This pretitration of chemical reducing agents, but not the biocide, then permits this test to be completed.

The bacteria which have been found to react to this test and which bacteria are commonly found in paper mills, cooling towers, and the like, have been found to include Pseudomonas, Bacillus, Klebsiella, Enterobacter, Escherichia, Sphaerotilus, Haliscomenobacter, in addition to many other bacterial genera. By using an appropriate choice of initial concentration of antimicrobial agents or biocide, it is possible to screen these biocides at concentration ranges from approximately 10,000 parts per million down to and including concentration below one part per million.

Our procedure has been nicknamed the Minitox selection process, and this Minitox selection test is presented in the following examples.

Figure 5:
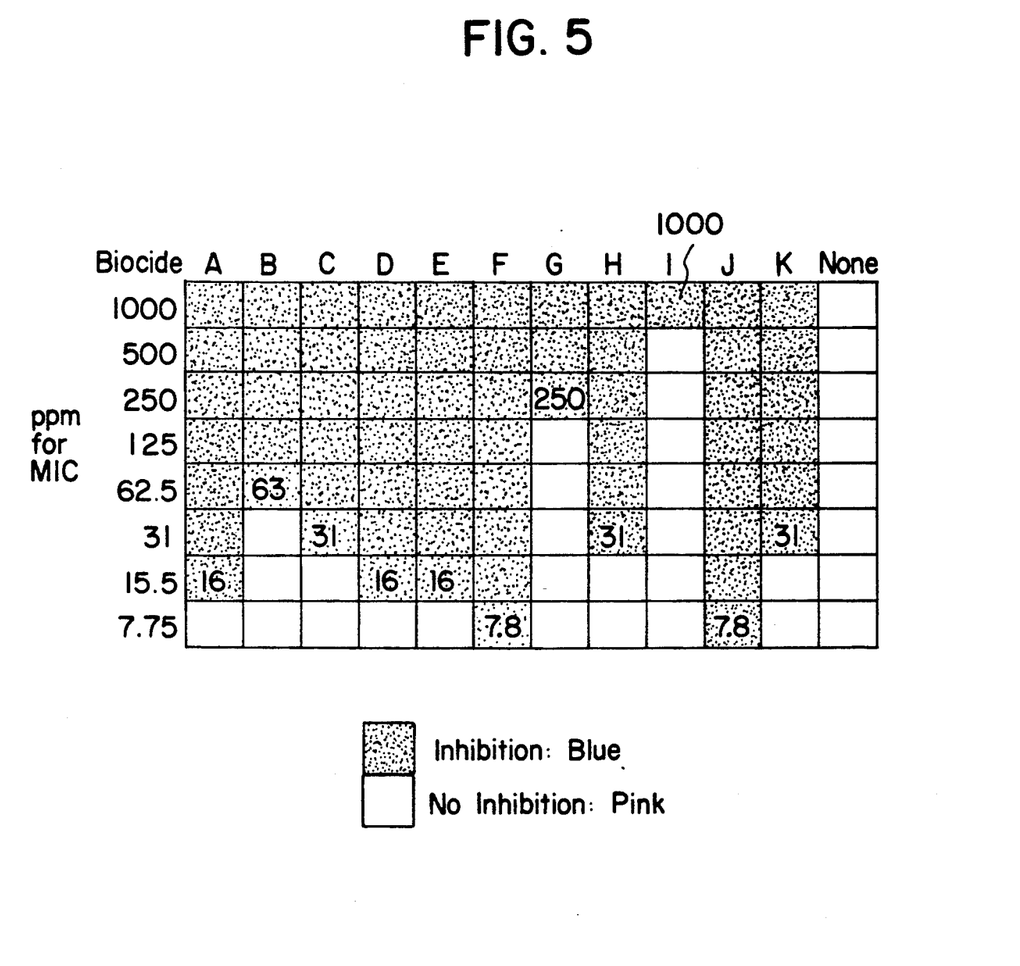
FIG. 5 shows the results that might be expected if a hypothetical microtitration plate containing biocides a through k were treated on a hypothetical paper machine furnish or other aqueous contamination source with each of the biocides at concentrations ranging from a high 1000 ppm to a low of approximately of 7.75 ppm by serially diluting according to the invention. After incubation the hypothetical biocides could provide the results indicated on this reacted microtitration grid and interpretation of this grid would show that biocide a would have a MIC of approximately 15.5 ppm, biocide b would have a MIC of approximately 62.5 ppm, biocide f would have a MIC of approximately 7.75 ppm, biocide i would have a MIC of approximately 1000 ppm, and biocide k would have a MIC of approximately 31 ppm. The other biocides would have appropriate MICs as read accordingly.

This hypothetical result is presented as means of fully and completely describing what is meant by the term "first change in color relative to the untreated column". As can be seen the first change in color is that first change where microbiological inhibition is observed at the dilution providing a continued blue color of the oxidized form of resazurin. Of course if other redox indicator dyes are used appropriate results, perhaps involving other colors and color changes, will be obtained.

Where no antimicrobial activity is observed, such as in the blank column labeled "none", microbiological activity will be rampant and all of the indicator dye will be converted to its reduced form, that is pink when using the resazurin dye system.

EXAMPLE 1

Minitox Test Recycle Newsprint Furnish

The Minitox product selection test was run on sample of white water furnish from a recycle newsprint papermachine. The standard procedure (set out above) was followed. The pH of the mill system was 7.0. The papermachine contained both numerous aerobic and anaerobic microorganisms. A Plate count on tryptone glucose extract agar showed the counts to be $4.4 \times 10^7$ colony forming units (cfu) per ml.

Figure 1:
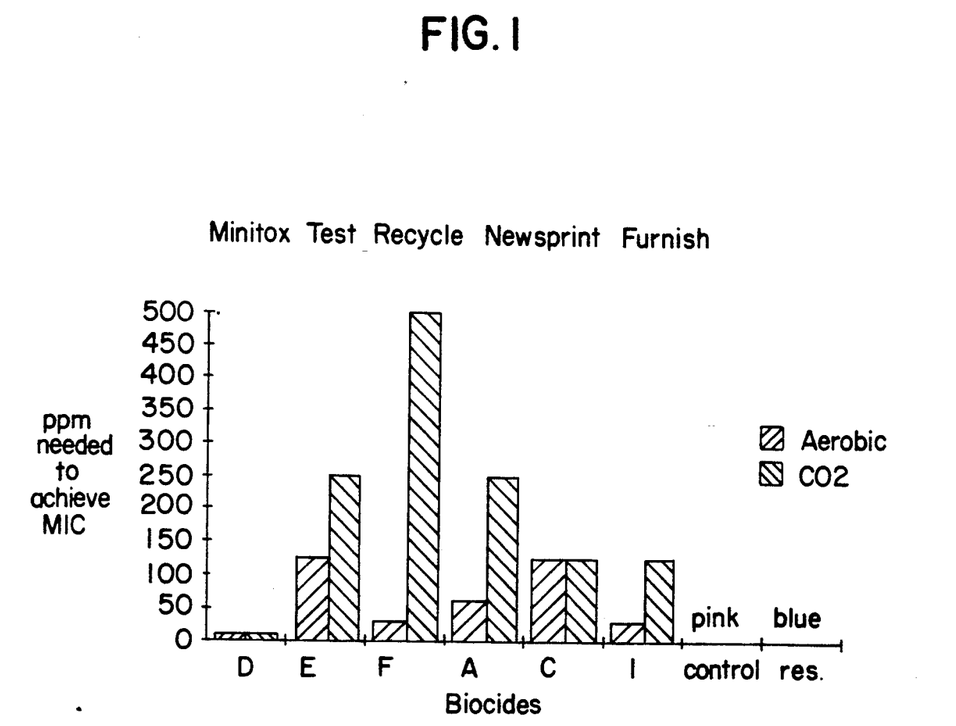
FIG. 1 shows the result of the use of the Minitox tests described on sample of paper furnish from a newsprint papermachine.

The Minitox test procedure outlined above was set up on duplicate microtitration plates with one set to be incubated in a standard atmosphere and the other in a $CO_2/N_2$ anaerobic environment generated in a BBL Gaspak. Control strips (columns) containing test paper furnish with the standard nutrients, dyes, but no biocide, were included with each microtitration plate. In addition, a control strip containing a resazurin solution without test paper furnish was also included. The results obtained are shown in FIG. 1.

EXAMPLE 2

Minitox Test on Recycle Container Mill Test Waters

Figure 2:
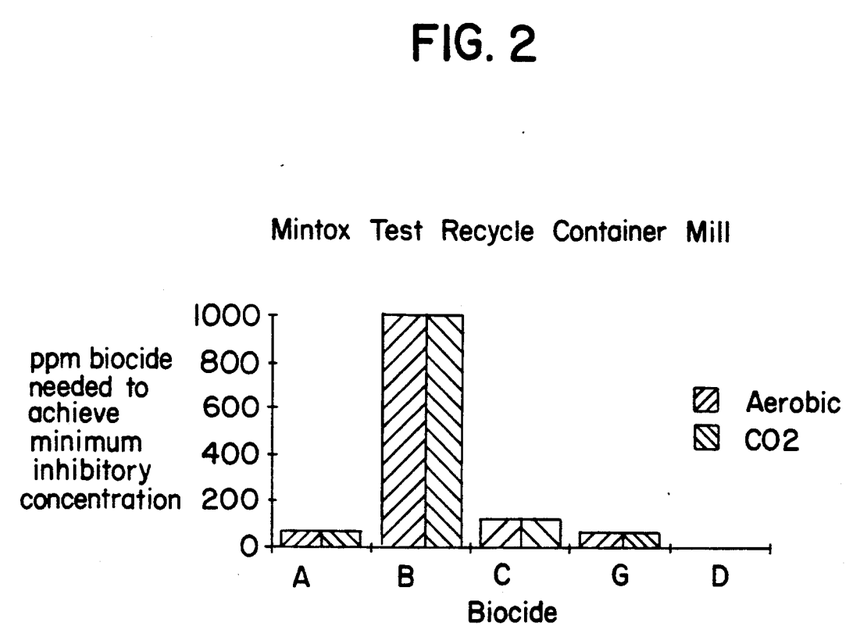
FIG. 2 shows the result of the minitox test procedure used on a sample from a recycled container board mill.

A sample from a recycle container board mill running at thermophilic temperatures was tested using the standard procedure. The pH of the system was at 7.8. The system contained numerous thermophilic and mesophilic bacteria. Incubation was conducted at 65° C. in both aerobic and $CO_2$ atmospheres. The results are shown in FIG. 2.

EXAMPLE 3

Minitox Test on Alkaline Coated Paper Water System

Figure 3:
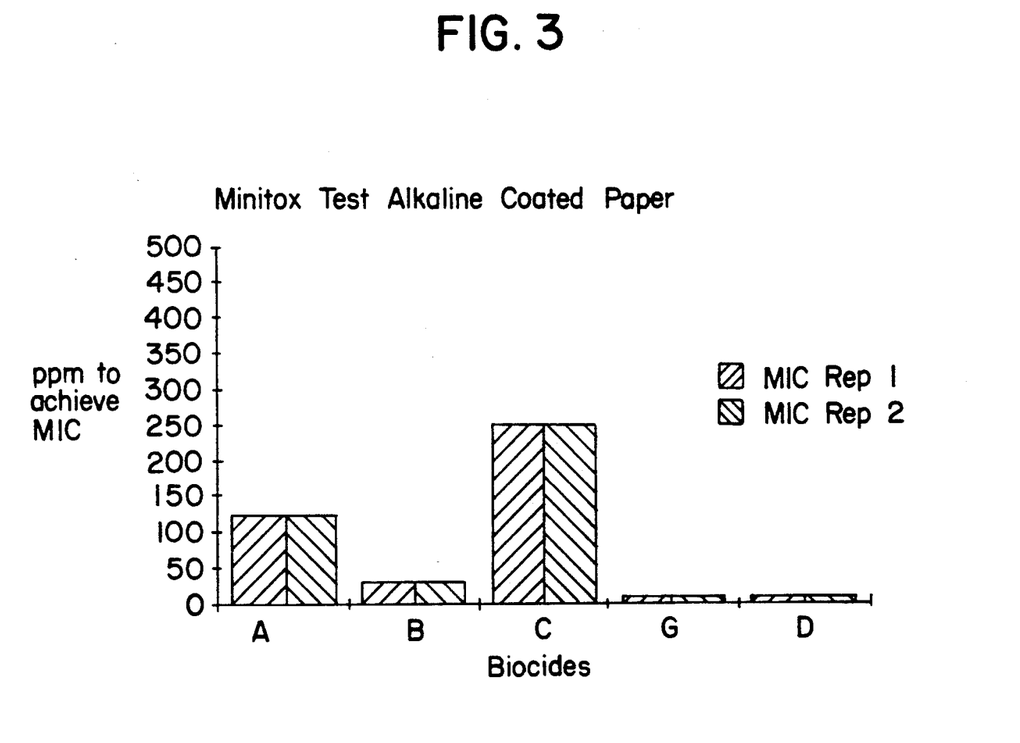
FIG. 3 shows the results of a minitox test result procedure used on a water sample obtained from a paper furnish from an alkaline coated paper system.

Furnish from an alkaline coated paper system was treated in the standard manner. The pH of the system was 7.5 and the plates formed were incubated aerobically. The results are shown in FIG. 3.

EXAMPLE 4

Figure 4:
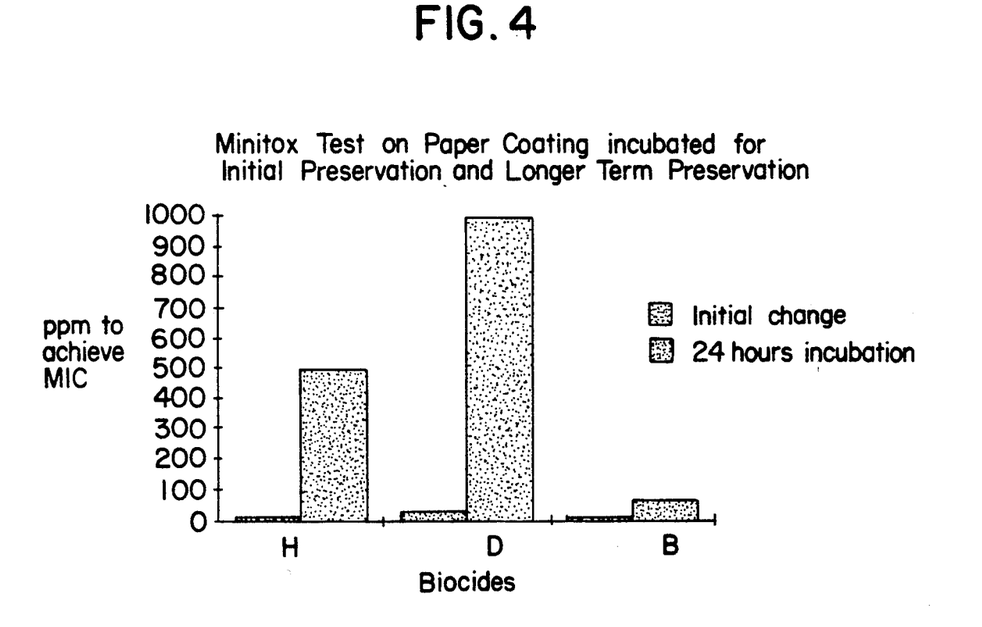
FIG. 4 shows the results of a minitox test procedure used on paper coating incubated for initial preservation and incubated for longer term preservation.

Minitox Test on Paper Coating Incubated for Initial Preservation and Longer Term Preservation Water samples from a coating sample were treated to run the Minitox test. In order to run the test in such a thick, highly pigmented material, it was necessary to dilute the material with the resazurin solution in nutrient broth (50 ml of coating plus 55 ml of resazurin solution). The test was run in the normal manner, however the wells were not backfilled before incubation. The microtitration plates were incubated aerobically. The results are shown in FIG. 4.

Representative of the type biocides which may be used or those biocides listed in Table I:

TABLE I

| Product | Possible Biocides* Structure of Active(s) | Type of Active(s) |
|---|---|---|
| H | $CH_3$-N, N-$CH_3$ ring with S, S | organosulfur |
| E | RNH~~NH$_2$.HOAC<br>R = Coco ($C_{6-12}$)alkyl | polyamine salt |
| F | N≡C—S—$CH_2$—S—C≡N | MBT methylene bis thiocyanate |
| A | RNH~~NH$_2$.HOAC +<br>$Cl_3$C—$SO_2$—$CCl_3$<br>R = Coco ($C_{6-18}$)alkyl | polyamine-sulfone combo |

TABLE I-continued

Possible Biocides*

| Product | Structure of Active(s) | Type of Active(s) |
|---|---|---|
| B | [isothiazolin structure with Cl, S, N-CH₃, =O] (1.15%); [isothiazolin structure with S, N-CH₃, =O] (0.35%) | isothiazolin |
| C | [benzyl-$CH_2$-$N^+(CH_3)(R)(R)$ $Cl^-$]<br>R = alkyl, alkyl (8%)<br>R = $CH_3$, alkyl (42%)<br>alkyl = $C_{14}$ 60%, $C_{16}$ 30%, $C_{12}$ 5%, $C_{12}$ 5% | quaternary amine |
| G | $N\equiv C-C(Br)(Br)-CONH_2$ | organobromine |
| D | $(CH_3)_2N-C(=S)-S^-Na^+$ +<br>$CH_2-NHC(=S)-S^-Na^+$<br>$CH_2-NHC(=S)-S^-Na^+$ | carbamate mixture |
| I | [benzothiazole]-S-$CH_2$-SCN +<br>$Cl_3C-SO_2-CCl_3$ | benzothiazole-sulfone combo |

*These biocides may also be used in any combination and other biocides may also be used subject only to proper safety, health, and environmental safeguards.

To test the regrowth of microorganisms and or biocide persistency, it is possible to modify the above test sequence by delaying the performance of step (b) above. The addition of the redox indicator dye may be delayed anywhere from about 30 minutes to about 20 hours. By doing so, the measurement of dehydrogenase enzyme is delayed which can permit the measurement, or at least the sensing of microbiological activity or at least the nutrient enhanced metabolic rate of microbiological growth in various time delayed sequence. This information can give the operator additional insight on not only the MIC but also information related to timing use of antimicrobial agents.

Having described my invention I claim:

1. A method of determining the minimum inhibitory concentration of an antimicrobial agent in a contaminated aqueous system selected from the group consisting of stock or furnished solutions from a pulp and paper manufacturer, waters from open recirculating cooling water systems, waste effluent streams, chemical process streams and fermentation streams, which contain microbiological organisms, comprising the steps of:
   (a) Obtaining a sample of said contaminated aqueous system;
   (b) Adding a reduction oxidation indicator dye to said sample which reacts with microorganisms producing dehydrogenase enzymes;
   (c) Adding dairy half and half creamer to said sample to form a dye treated nutrient aqueous system;
   (d) Obtaining aliquots of the dye treated nutrient aqueous system;
   (e) Performing multiple serial dilutions of an antimicrobial agent to be tested and forming mixtures of said aliquots of the dye treated nutrient aqueous system with each of the said serial dilutions;
   (f) Incubating said mixtures at a temperature essentially equivalent to the temperature of the contaminated aqueous system for a period of time sufficient to develop the change in the dye color by the reaction of the dye with reducing enzymes; and
   (g) Determining the minimum inhibitory concentration of antimicrobial agent that inhibits those microbial organisms contained in said contaminated aqueous system by observing a change in color.

2. The method of claim 1, wherein step (c) further comprises adding a nutrient selected from the group consisting of glucose, sucrose, beef extract, peptone, tryptone, milk, yeast extract, and mixtures thereof.

3. The method of claim 1, wherein the steps are performed in the order (a) through (g).

4. The method of claim 1 wherein the serial dilutions are performed so that the final concentrations of said antimicrobial agents in the serial dilutions comprise concentrations ranging from about 0.1 parts per million to about 0.1 parts per million, on the basis of the total volume of the dye treated, nutrient treated aqueous system.

5. The method of claim 1 wherein steps (b) and (c) are performed, in any sequence thereof, and may be performed after any of steps (a), (d), and (e).

6. The method of claim 1, wherein the reduction-oxidation indicator dye is chosen from the group consisting of tetrazolium violet, 2-(p-Iodophenyl)-3-(p-nitrophenyl)-5-phenyl-tetrazolium chloride, and resazurin and further wherein the pH of the dye treated nutrient aqueous system is adjusted to between 4.0 and 9.0.

7. The method of claim 1 wherein said serial dilutions of said dye treated nutrient aqueous system are incubated on a micro titration plate containing at least four columns of at least eight wells each, and the incubation is performed at a temperature within the range of from about 25° C. to about 60°0 C. and for a time period within the range of from about 60 minutes to about eight hours.

8. The method of claim 7 wherein during incubation an atmosphere containing predominantly an inert gas is maintained over the treated titration plate.

9. The method of claim 8 wherein the inert gas is chosen from the group consisting of $CO_2$ and $N_2$.

10. The method of claim 9 wherein the inert gas is $CO_2$ and the treated aqueous system is buffered to a pH ranging between 5.0 and 8.0.

11. The method of claim 1 wherein step (b) is delayed from 30 minutes to 20 hours.

* * * * *